United States Patent [19]

Mattei et al.

[11] 4,440,789

[45] Apr. 3, 1984

[54] SYNTHETIC ABSORBABLE HEMOSTATIC COMPOSITION

[75] Inventors: Frank V. Mattei, Piscataway, N.J.; Namassivaya Doddi, Upland, Calif.

[73] Assignee: Ethicon, Inc., Somerville, N.J.

[21] Appl. No.: 442,217

[22] Filed: Nov. 16, 1982

[51] Int. Cl.³ .................. A61K 31/74; C08G 63/08
[52] U.S. Cl. ..................... 424/78; 528/354
[58] Field of Search .............. 424/78; 528/354, 357

[56] References Cited

U.S. PATENT DOCUMENTS

| | | | |
|---|---|---|---|
| 2,772,999 | 12/1956 | Masci et al. | 424/180 |
| 3,021,316 | 2/1962 | Cox et al. | 528/354 X |
| 3,190,858 | 6/1965 | Cox et al. | 528/354 X |
| 3,395,217 | 7/1968 | Statt | 424/81 |
| 3,645,941 | 2/1972 | Snapp et al. | 528/354 X |
| 4,052,988 | 10/1977 | Doddi | 128/335.5 |
| 4,186,448 | 2/1980 | Brekke | 128/92 |

FOREIGN PATENT DOCUMENTS 1584080 2/1981 United Kingdom.

OTHER PUBLICATIONS

Annals of Surgery, vol. 132, 1950, pp. 1128–1130, New Absorbable Hemostatic Bone Wax, Drs. Geary and Frantz.

*Primary Examiner*—Leonard Schenkman
*Attorney, Agent, or Firm*—Leonard Kean

[57] ABSTRACT

A synthetic absorbable hemostatic composition for use in the control of osseous hemorrhage, comprising polydioxanone in a biocompatible base, the polydioxanone having a sufficiently low inherent viscosity such that the composition possesses a putty-like consistency at room temperature. The preferred composition is one in which the polydioxanone comprises between 65% and 75% by weight of the composition.

14 Claims, No Drawings

SYNTHETIC ABSORBABLE HEMOSTATIC COMPOSITION

BACKGROUND OF THE INVENTION

1. Field of the Invention

This invention relates to a bone sealant and more particularly to a synthetic absorbable hemostatic composition comprising polydioxanone in a biocompatible base, the polydioxanone having a sufficiently low molecular weight such that the composition possesses a putty-like consistency at room temperature. This invention also relates to a process for applying the bone sealant.

2. Description of Prior Art

Various substances and compositions have been employed by members of the medical profession to control bleeding from cut bone surfaces. One class of materials used for the control of this type of hemorrhage is called bone wax. Bone waxes are used for the purpose of controlling hemorrhages from the cut surfaces of bones, such as those of the skull, by forcibly smearing the wax over the cut surface so that the material acts mechanically to occlude and seal the open ends of the bleeding osseous vessels and sinuses.

Bone waxes used in surgery today are generally prepared from refined beeswax which has been admixed with other nonabsorbable and water insoluble hydrocarbons and vegetable oils. Certain disadvantages inhere in these bone wax compositions, as for example, relatively poor adhesion properties and the hard brittle state of the wax at room temperatures requiring use at elevated temperatures. Furthermore, paraffin based commercial bone wax is not absorbed by the body and thus remains at the site of application for long periods of time. As a result the wax acts as a foreign body, tending in some instances to make it difficult for the body to fight infection and inflammatory reactions that may be introduced in the surrounding tissue, and it also interferes with bone regrowth.

In order to overcome the latter problem, British Pat. No. 1,584,080 discloses an absorbable hemostatic bone sealant, which contains the active components collagen and fibrin. However, the composition of British Pat. No. 1,584,080 suffers from the disadvantage that its storage conditions must be controlled in order to retain desirable aesthetic and tactile properties since biological materials of animal origin are used.

U.S. Pat. No. 3,395,217 discloses nonabsorbable bone wax compositions comprised of low molecular weight ethylene copolymer waxes containing from about 15 to about 40 percent by weight of another unsaturated constituent and having molecular weights in the range of 1000 to 4000. These waxes have a semisolid consistency such that they can be kneaded between the fingers when at room temperature and have the right amount of tack and adhesion so that they can be easily manipulated in the hands of the surgeon or applied by any suitable applicator such as a gloved finger, spatula or appropriate disposable applicator.

U.S. Pat. No. 2,722,999 describes an absorbable bone wax comprised of a water soluble innocuous base and free acid cellulose glycolic acid ether or free acid cellulose hydroxypropionic acid ether as a hemostatic agent. The composition also preferably contains a tackifier such as cellulose glycolic acid ether salt or cellulose hydroxypropionic acid ether salt (preferably sodium salt) and water as a plasticizer. It is to be noted that cellulose and its derivatives are generally not biologically degradable, but merely soluble, and if the molecular weights are high enough may not even pass through the kidneys.

The Annals of Surgery 132, 1128 (1950) describes an absorbable hemostatic bone wax containing powdered oxidized cellulose as the hemostatic agent in a base of polyethylene glycol. The base is a mixture of high and low molecular weight polyethylene glycols selected to provide the malleability and consistency of material desired for this use. However, polyethylene glycols are completely water soluble. When they comprise the largest percentage of the mixture, the mixture becomes slimy in the area wet with tissue fluids, this being true of any water soluble base. In addition, some polyethylene glycols give a pronounced tissue reaction.

U.S. Pat. No. 4,186,448 discloses a one-piece molded body member for filling and covering a bone void or soft tissue deficiency, which body member attracts blood in fluid suspension by capillary action until clotting forms which ultimately leads to the formation of tissue and/or bone. The body member is made of a biodegradable material such as polylactic acid.

The present invention provides a new synthetic absorbable bone sealant which is a putty-like semisolid at room temperature. The softness of the sealant allows the material to be packaged in a syringe, plastic or coated paper envelope, or aluminum or glass tube from which it may be extruded or dispensed in desired amounts during use. The sealant has sufficient tack so that it adheres to bone surfaces, yet is easily manipulated in the hands of the surgeon without crumbling or sticking to the surgeon's gloves.

Considering that dioxanone polymers are normally solid, hard materials, it is surprising that the instant polydioxanone, in conjunction with the base, possesses the above described putty-like properties. In fact, the instant polydioxanone possesses unexpected properties and opens a field of application quite different from those of the original higher molecular weight precursors.

The instant composition, being primarily based upon the synthetic material polydioxanone, maintains a desirable aesthetic physical appearance even after long periods of standing. Furthermore, the instant composition possesses all of those properties, most desirable in a bone wax, namely consistency, set-up, smearability and translucency.

It is to be noted also that known sutures prepared from poly-p-dioxanone polymers having higher molecular weights, have an established profile of in vivo absorbability (see U.S. Pat. No. 4,052,988). Thus the polydioxanone of very low molecular weight, such as that utilized in the present bone wax, must clearly be even more absorbable in vivo.

SUMMARY

The bone sealant of the present invention comprises between about 60% and 85% by weight of polydioxanone in a biocompatible base, the polydioxanone having a sufficiently low molecular weight such that it is workable and softenable by hand to bring about a putty-like consistency at room temperature. The sealant has a consistency of a semisolid which is extrudable from a large orifice syringe. The sealant is packaged in a syringe, plastic envelope or aluminum tube and sterilized by radiation. During use, small amounts of the sealant may be extruded from the package as required by the surgeon. The sealant is effective to control osseous hemorrhage from cut bone and does not interfere with subsequent healing and rejoining of bone parts.

DESCRIPTION OF PREFERRED EMBODIMENTS

The polydioxanone used in the composition of the present invention possesses an inherent viscosity range between 0.03 and 0.15 (and is preferably about 0.1). The polydioxanone, in conjunction with a suitable base, is workable and softenable by hand to bring about a desired putty-like consistency at room temperature, permitting a surgeon to spread the agent with his fingers or a spatula over the cut surface of a bone. At the same time, the agent has a tackiness which permits it to adhere readily to the bleeding bone surface and yet being able to be manipulated without crumbling or sticking to the surgeon's gloves.

The biocompatible base (consisting of natural or synthetic oils and waxes) utilized in the present composition is preferably selected from the group consisting of isopropyl palmitate, triglycerides (such as sesame oil, almond oil, castor oil), ethylene oxide/propylene oxide block copolymers, polyethylene glycols and methoxypolyethylene glycols. Preferably, the polydioxanone comprises between 65% and 75% by weight of the composition, the polydioxanone being present in the form of a finely pulverized powder having a particle size of less than 200 microns. The preferred composition is one in which the base is sesame oil and the polydioxanone comprises about 65% to 75% (most preferably 68% by weight of the composition). In this case, the inherent viscosity of the polydioxanone varies between about 0.03 and 0.15.

The preferred emollients used are Deltyl Prime (a trademark for isopropyl palmitate); sesame oil; castor oil; almond oil; Carbowax 400 (a trademark for certain polyethylene glycols and methoxypolyethylene glycols) and Pluronic P84 (a tradename for ethylene oxide/propylene oxide block copolymers).

In order to homogenize the composition, a two component solution, involving little or no chemical change is ideally desired. The first method of doing so would be to stir a molten liquid of the two components. Overall this method is relatively unsuccessful since the oily emulsion, present during heating tends to be followed by a phase separation which indicates the possibility of chemical reaction or non-uniformity.

A second, more successful method consists of mechanical mixing by means of mortar and pestle. By means of this method of mechanical mixing, the proper consistency, set-up and smearability are attained. The low molecular weight polydioxanone is quite resistant to pulverization and it is therefore necessary to grind it to a fine powder before mixing the two components. Applicant has found that the compounding process is aided by heating the emollient (preferably for about thirty minutes in a 70° C. oven) prior to mixing and then heating the mixture (overnight in a 80° C. oven). On an industrial scale, the pulverization process may be achieved by using a dough mixer and some means of applied pressure (i.e. piston action). A three roll mill as used in dispersing pigments in protective coatings would be ideal. Rather than metal, the rolls should be of porcelain or ceramic.

Applicant has found that the instant bone wax possesses the most desirable properties when the polydioxanone-emollient ratio is approximately 70/30.

Table 1 sets forth consistency and tactile properties of the instant compositions. It will be noted from Table 1 that the polydioxanone-sesame oil composition provides the most desirable properties of those compositions listed in the Table. Applicant has also found that sterilization with Cobalt-60 has no adverse effect on the consistency and tactile properties of any of the compositions of Table 1.

In Vivo Studies

Tissue reaction and efficacy studies were carried out as summarized in the following Tables 2, 3 and 4.

The tests were carried out in rats to determine the tissue reaction evoked by the various materials. Three rats were used per sample and the material was either implanted or injected into the ventral subcutis. If the material was solid, approximately 1 cm × 1 cm squares were implanted; if the material was in the form of granules or powder, two scoopfuls, using a small flat spatula, were placed in a subcutaneous pocket; and if the materials were liquid, 0.25 ml of the liquid was injected into the subcutis. The rats were examined after twenty-four hours and usually one rat was killed at this time. The remaining rats were observed for seven days, whereafter they were killed. The implant sites were then exposed and characterized. These characterizations are set forth in Tables 2, 3 and 4.

As will be noted from Table 2, after seven days, essentially none of the single components gave evidence of irritation. However, this is not true of the observations at twenty-four hours, which vary more widely. Furthermore, the washed polydioxanone polymer showed a minimal reaction, whereas the unwashed polydioxanone incurred extensive irritation. As will be noted from Table 3, the two compositions based upon Deltyl Prime or sesame oil with polydioxanone exhibited no adverse tissue reaction, while the remaining two had unfavorable reactions. It should be noted, however, that Carbowax 400 was reported as having no adverse tissue reaction when injected individually; however, as a component of bone wax the reaction was pronounced.

Evaluation of Surgical Efficacy

The following evaluation of surgical efficacy was carried out:

Four craniotomy holes, 7 mm in diameter were made through the bone down to the dura on a beagle dog cadaver. A different wax sample was implanted in each hole and the characteristics of the wax evaluated. The results were as follows:

Least Desirable—Polydioxanone/Pluronic P84
Moderately Desirable—Polydioxanone/Deltyl Prime
  Polydioxanone/Carbowax 400
Most Desirable—Polydioxanone/Sesame Oil The above observations were mostly a qualitative measure of surgical efficacy. Of course, these observations do not relate to the hemostatic ability of the bone waxes. Although it was observed that the adhesive properties of the samples were less than desirable, they were nevertheless considered suitable for their intended use on the basis of their other physical and in vivo properties.

The present invention also includes within its ambit polydioxanone which has an inherent viscosity in hexafluoroisopropanol at a concentration of 0.1 dl/g and at a temperature of 25° C., of between about 0.03 and 0.15.

Also included within the scope of the present invention is the process for the control of bleeding from cut bone surfaces, which comprises applying to the cut bone surface a hemostatic composition comprising from 60% to 80% by weight of polydioxanone in a biocompatible base, said polydioxanone having a sufficiently low molecular weight such that the mixture with a base is workable and softenable by hand to bring about a putty-like consistency at room temperature and having a tackiness sufficient for it to adhere readily to a bloody bone surface and yet being able to be manipulated without sticking to the surgeon's gloves.

The present process is preferably carried out utilizing a composition in which the polydioxanone comprises between 65% and 75% by weight of the composition and the base is selected from the group consisting of isopropyl palmitate, sesame oil, almond oil, castor oil and ethylene oxide/propylene oxide block copolymers, polyethylene glycols and methoxypolyethylene glycols.

The present process is most preferably carried out utilizing a composition in which the base is sesame oil and the polydioxanone comprises about 68% by weight of the composition, the inherent viscosity of the polydioxane being approximately 0.1.

Polymerization Procedure

The polydioxanone utilized in compositions of the present invention is prepared by the polymerization of p-dioxanone monomer in a conventional manner using a polymerization reactor equipped with heating and stirring means and in the presence of a polymerization catalyst such as stannous octoate. A suitable chain terminator, such as lauryl alcohol, is used in order to limit the molecular weight to a very low level. The polymerization is conducted with pure and dry reactants and under an atmosphere of dry nitrogen at a temperature sufficient to maintain the reaction mixture in a molten state until the polymerization is complete.

Specific details concerning the polymerization are set forth in the following examples.

The following examples are provided to further illustrate preferred embodiments of the present invention.

EXAMPLE 1

Low Molecular Weight Polydioxanone

| Component | Amount | % by Weight | Moles |
|---|---|---|---|
| p-Dioxanone Monomer (Purified) | 600.0 g. | 75 | 5.85 |
| Dodecanol | 200.0 g. | 25 | 1.07 |
| Stannous Octoate (Catalyst), 0.33 molar Solution in Toluene | 1.19 ml | — | $3.93 \times 10^{-4}$ |

Monomer to Catalyst Ratio = 15,000/1

The above monomer, dodecanol and catalyst are transferred into a 1000 ml glass ampoule containing a magnetic stirring bar and the ampoule is then pumped down to a vacuum of about $100\mu$. The vacuum is then alternated with nitrogen purges about three times, and the ampoule is finally sealed at about 7-10 inches nitrogen/vacuum. The polymerization is then carried out in an oil bath equipped with a magnetic stirrer under it for about eight hours at 120° C. The ampoule is then cooled and the polymer is then removed from the ampoule. The resultant polymer has a very waxy consistency and is unlike any polydioxanone polymer previously known. The product has hand-workability properties suitable for a bone wax.

Purification Procedure

In view of the fact that the above low molecular weight polydioxanone may contain unreacted monomer as well as dodecanol, said polymer is cleaned by extracting several times with methanol. The methanol extract is filtered off and discarded while the cleaned-up polymer is dried in vacuum for several days to constant weight. The melting range is about 80°-92° C., while the inherent viscosity in hexafluoroisopropanol at a concentration of 0.1 g/dl and at a temperature of 25° C., is about 0.1.

EXAMPLE 2

Seventy to eighty parts of the polydioxanone, purified according to the procedure of Example 1 are mixed with about 20 to 30 parts of either sesame oil or isopropyl palmitate, Carbowax 400, castor oil, almond oil, or Pluronics F-68 (details of which are set forth in Table 1). The resulting mixtures possess the desirable consistency and tactile properties of a good bone wax. Methods of mixing include heating, or mortar and pestling, or a combination of these. A dough mixer of adequate power and appropriate size is ideal in this connection.

TABLE 1

SYNTHETIC ABSORBABLE BONE WAX
Consistency & Tactile Properties of PD* Based Compositions**

| Composition: | Deltyl Prime 29% | Sesame Oil 31.8% | Carbowax 400 25.3% | Pluronic P84 31.8% |
|---|---|---|---|---|
| Means of Mixing | (1) pulverize PDS polymer; (2) heat plasticizer to ~70° C.; (3) heat pulverized mixture in 80° C. oven overnight; (4) pulverize | | | |
| Consistency | smooth, soft | smooth (some lumps)*** soft, slightly sticky | smooth, soft sticky when worked up | v. hard ↓ v. sticky when worked up |
| Appearance | white, semi-translucent | off-white, semi-translucent | white, semi-translucent | white, semi-translucent |
| Greasiness | waxy | waxy | waxy | waxy |
| Smearability | good (some cracking) | v. good | v. good | v. good |
| Odor | burnt | burnt | slight | burnt |
| Quantity | 5 g. | 50 g. | 50 g. | 50 g. |
| Relative Rating**** | 3 | 1 | 2 | 4 |

TABLE 1-continued

SYNTHETIC ABSORBABLE BONE WAX
Consistency & Tactile Properties of PD* Based Compositions**

| Composition: | Deltyl Prime 29% | Sesame Oil 31.8% | Carbowax 400 25.3% | Pluronic P84 31.8% |
|---|---|---|---|---|
| Viscosity***** | 3493 | | 3954 | |

*PD - Poly p-dioxanone of very low mol. wt. IV = 0.1 (dl/g in hexafluoroisopropanol at 25° C. Concentration 0.1 g/dl)
**Observations before sterilization.
***It is likely that lumpiness is due only to the degree of pulverization prior to mixing
****On a subjective scale of 1–5, 1 is the best while 5 is the worst.
*****Shear Rate 228.5, Temp. 35° C., Instron Rheometer.

TABLE 2

SYNTHETIC ABSORBABLE BONE WAX
Results of Tissue Reaction to Individual Sterile Components

| Component | Package | Air or $N_2$ | Sterilization $^{60}Co$, mR | Results (ventral subcutis) Rats 1 Day | 7 Days |
|---|---|---|---|---|---|
| Deltyl Prime | vial | $N_2$ | 2.5 | No Adverse Tissue Reaction (NATR), slight congestion & edema at periphery of encapsulated fluid. | NATR, small amount of injected fluid remained. |
| Sesame Oil | vial | $N_2$ | 2.5 | | Transparent jelly-like mass on skin side containing clear oil fluid. |
| Carbowax 400 | vial | $N_2$ | 2.5 | No adverse Rxn in live rat. | NATR, no evidence of injected material. |
| Pluronic F68 +4–5% $H_2O$ | P.E. sleeve-then foil pouch | Air | 2.5 | Extensive edema, Systemic Effects: lethargic, anal area wet, paws tinged with blood. | NATR, Rats appeared in good health, material completely absorbed. |
| Dodecanol | none | Air | none | All sides edematous. Large firm palpable masses developed. | Mass incised, oily fluid with odor of lauryl alcohol exposed. No differences among three samples. |
| | vial | $N_2$ | 2.5 | | |
| | vial | Air | 2.5 | | |
| Almond Oil PD* Bone Wax Washed | vial | $N_2$ | 2.5 | | NATR NATR, granules thinly encapsulated. |

*PD - Poly p-dioxanone of very low molecular weight I.V. = 0.1

TABLE 3

SYNTHETIC ABSORBABLE BONE WAX
Results of Tissue Reaction to Implanted Bone Wax Compositions

| Composition | Wt. % | Results After 7 Day Implantation (Ventral Subcutis) Rats |
|---|---|---|
| PD* | 71 | No adverse tissue reaction. Bone wax intact. |
| Deltyl Prime | 29 | |
| PD* | 68.2 | No adverse tissue reaction. Bone wax intact, v. thin |
| Sesame Oil | 31.8 | capsule in one rat and slight hemorrhage in another. |
| PD* | 74.7 | Bone wax thickly encapsulated with bloody fluid. White |
| Carbowax 400 | 25.3 | spongy mass, which appeared to be bone wax encapsulated with fluid. Bone wax discolored. |
| PD* | 68.2 | Bone wax moderately encapsulated with clear fluid. |
| Pluronic P84 | 31.8 | White granular material dispersed in capsule. |

*PD - Poly p-dioxanone of very low molecular weight I.V. = 0.1
Twenty 1 gram samples of each of the 4 candidates were packaged and sterilized for toxicity studies. The packaging involves placing bone wax pellet in polyethylene sleeve (sealed on 3 sides), then inserting the sleeve in a foil pouch and sealing under nitrogen. Fifteen packages receive 2.5 Mrads of $^{60}Co$ sterilization while 5 were kept as control. All implanted samples were sterile.

TABLE 4

SYNTHETIC ABSORBABLE BONE WAX
Select Candidates. Summary of Aesthetic, Tissue Reaction & Surgical Use Properties

| Composition | Wt. % | Consistency* | Tissue Reaction in Rats (See Table 3 for Details) |
|---|---|---|---|
| PD* | 71 | 4 | NATR. Bone wax intact. |
| Deltyl Prime | 29 | | |
| PD* | 68.2 | 5 | NATR. Bone wax intact. |
| Sesame Oil | 31.8 | | |
| PD* | 74.7 | 5 | Bone wax thickly encapsulated with bloody fluid. |
| Carbowax 400 | 25.3 | | White, spongy mass, appeared to be bone wax encapsulated with fluid. Bone wax discolored. |
| PD* | 68.2 | 2 | Bone wax moderately encapsulated with clear |
| Pluronic P84 | 31.8 | | fluid. White, granular material dispersed in |

TABLE 4-continued

SYNTHETIC ABSORBABLE BONE WAX
Select Candidates. Summary of Aesthetic, Tissue Reaction & Surgical Use Properties

| Composition | Wt. % | Consistency* | Tissue Reaction in Rats (See Table 3 for Details) |
|---|---|---|---|
| | | | capsule. |

All samples packaged and sterilized, see Table 3.
Scale 1-5, 5 best, 1 worst.
*PD - Poly p-dioxanone of very low molecular weight I.V. = 0.1

We claim:

1. A synthetic body absorbable hemostatic composition for use in the control of osseous hemorrhage, comprising from 60% to 80% by weight of purified polydioxanone in a biocompatible base, said polydioxanone having an inherent viscosity in hexafluoroisopropanol at a concentration of 0.1 g/dl and at a temperature of 25° C. of between about 0.03 and 0.15, said base comprising a natural or synthetic oil or wax which is absorbable in the body, said polydioxanone having a sufficiently low inherent viscosity such that the mixture with the base is workable and softenable by hand to bring about a putty-like consistency at room temperature and having a tackiness sufficient for it to adhere readily to a bloody bone surface and yet being able to be manipulated without crumbling or sticking to the surgeon's gloves.

2. The composition of claim 1, in which the base is selected from the group consisting of isopropyl palmitate, sesame oil, castor oil, almond oil, ethylene oxide/propylene oxide block copolymers, polyethylene glycols and methoxypolyethylene glycols.

3. The composition of claim 1 in which the polydioxanone comprises between 65% and 75% by weight of the composition.

4. The composition of claim 2 in which the inherent viscosity of the polydioxanone is about 0.1.

5. The composition of claim 3 in which the polydioxanone is present in the form of a finely pulverized powder having a particle size of less than 200 microns.

6. The composition of claim 5 in which the base is sesame oil and the polydioxanone comprises about 68% by weight of the composition.

7. A synthetic body absorbable hemostatic composition for use in the control of osseous hemorrhage, comprising from 65% to 75% by weight of purified polydioxanone in a body absorbable biocompatible base, said polydioxanone having an inherent viscosity in hexafluoroisopropanol at a concentration of 0.1 g/dl and at a temperature of 25° C. of between about 0.03 and 0.15, said base being selected from the group consisting of isopropyl palmitate, triglycerides, ethylene oxide/propylene oxide block copolymers, polyethylene glycols and methoxyethylene glycols, said polydioxanone having a sufficiently low inherent viscosity such that the mixture with the base is workable and softenable by hand to bring about a putty-like consistency at room temperature and having a tackiness sufficient for it to adhere readily to a bloody bone surface and yet being able to be manipulated without crumbling or sticking to the surgeon's gloves.

8. The composition of claim 7 in which the base is a triglyceride.

9. A synthetic absorbable hemostatic composition for use in the control of osseous hemorrhage comprising by weight 65% to 75% purified polydioxanone and 25% to 35% by weight of sesame oil, said polydioxanone having an inherent viscosity in hexafluoroisopropanol at a concentration of 0.1 g/dl and at a temperature of 25° C. of between about 0.03 and 0.15.

10. A process for the control of bleeding from cut bone surfaces, which comprises applying to the cut bone surface a body absorbable hemostatic composition comprising from 60% to 80% by weight of purified polydioxanone in a biocompatible base, said polydioxanone having an inherent viscosity in hexafluoroisopropanol at a concentration of 0.1 g/dl and at a temperature of 25° C. of between about 0.03 and 0.15, said base comprising a natural or synthetic oil or wax which is absorbable in the body, said polydioxanone having a sufficiently low inherent viscosity such that the mixture with the base is workable and softenable by hand to bring about a putty-like consistency at room temperature and having a tackiness sufficient for it to adhere readily to a bloody bone surface and yet being able to be manipulated without crumbling or sticking to the surgeon's gloves.

11. The process of claim 10 in which the base is selected from the group consisting of isopropyl palmitate, sesame oil, castor oil, almond oil, ethylene oxide/propylene oxide block copolymers, polyethylene glycols and methoxypolyethylene glycols.

12. The process of claim 11 in which the polydioxanone comprises between 65% and 75% by weight of the composition.

13. The process of claim 12 in which the polydioxanone is present in the form of a finely divided powder having a particle size of less than 200 microns.

14. A process for the control of bleeding from cut bone surfaces, which comprises applying to the cut bone surface a hemostatic composition comprising from 65% to 75% by weight of purified polydioxanone in a body absorbable biocompatible base, said polydioxanone having an inherent viscosity in hexafluoroisopropanol at a concentration of 0.1 g/dl and at a temperature of 25° C. of between about 0.03 and 0.15, said base being selected from the group consisting of isopropyl palmitate, triglycerides, ethylene oxide/propylene oxide block copolymers, polyethylene glycols and methoxyethylene glycols, said polydioxanone having a sufficiently low inherent viscosity such that the mixture with the base is workable and softenable by hand to bring about a putty-like consistency at room temperature and having a tackiness sufficient for it to adhere readily to a bloody bone surface and yet being able to be manipulated without crumbling or sticking to the surgeon's gloves.

* * * * *